United States Patent [19]

Hofreiter et al.

[11] 4,121,974

[45] Oct. 24, 1978

[54] PREPARATION OF RETROGRADATION-RESISTANT STARCHES WITH IMMOBILIZED AMYLASES

[75] Inventors: Bernard T. Hofreiter, Peoria; Karl L. Smiley, Morton; Joyce A. Boundy, East Peoria, all of Ill.

[73] Assignee: The United States of America as represented by the Secretary of Agriculture, Washington, D.C.

[21] Appl. No.: 811,398

[22] Filed: Jun. 29, 1977

[51] Int. Cl.² ............................................. C12D 13/02
[52] U.S. Cl. ..................................... 195/7; 195/31 R; 195/115
[58] Field of Search .................... 195/47, 31 R, 63, 68, 195/DIG. 11, 115

[56] References Cited

U.S. PATENT DOCUMENTS

| | | | |
|---|---|---|---|
| 3,849,253 | 11/1974 | Harvey et al. | 195/68 |
| 4,011,137 | 3/1977 | Thompson et al. | 195/31 R |
| 4,013,514 | 3/1977 | Wildi et al. | 195/31 R |

OTHER PUBLICATIONS

Boundy et al., "Exoenzymic Activity of Alpha-Amylase Immobilized on a Phenol-Formaldehyde Resin", *Carbohydrate Research*, vol. 48, (1976), pp. 239-244.

Olson et al., "Lactase and other Enzymes bound to a Phenol-Formaldehyde Resin with Glutaraldehyde", *Journal Agr. Food Chem.* vol. 21, No. 3, (1973), pp. 440-445.

Barker et al., "Enzyme Reactors for Industry", *Process Biochemistry*, vol. 6, No. 10 (1971), pp. 11-12.

*Primary Examiner*—Thomas G. Wiseman
*Attorney, Agent, or Firm*—M. Howard Silverstein; David G. McConnell; Curtis P. Ribando

[57] ABSTRACT

Retrogradation-resistant starches of reduced molecular linearity are produced by preferentially hydrolyzing the amylose component of ordinary starches with amylases immobilized on porous carriers which are preferentially sorptive to amylose over amylopectin.

11 Claims, No Drawings

PREPARATION OF RETROGRADATION-RESISTANT STARCHES WITH IMMOBILIZED AMYLASES

BACKGROUND OF THE INVENTION

1. Field of the Invention

This invention relates to controlling the hydrolytic specificity of amylases by immobilization on a carrier and to the use of these immobilized enzymes in the preparation of retrogradation-resistant starches of reduced molecular linearity.

2. Description of the Prior Art

The stability of aqueous starch dispersions often determines their acceptance in many industrial and food applications. The extent of retrogradation of starch pastes is related inversely to temperature and directly to concentration. At room temperature, gelling or precipitation may readily occur in corn starch dispersions of moderate, e.g., 2%, concentration. It is generally recognized that amylose, the linear molecular component of starch, is chiefly responsible for this phenomenon. Consequently, starches that consist exclusively of branched amylopectin, such as those derived from waxy varieties of corn or sorghum grain, have been used where amylose crystallization, either during or after an application, is a disadvantage. The more costly waxy starches differ in rheological properties from ordinary starches having amylose contents in the range of 17–28%. Alternatives for preparing stable amylaceous dispersions have included use of amylopectin obtained by starch fractionation, chemical derivatives and modifications of starch (e.g., hydroxyethyl ether and oxidized starches) that minimize amylose retrogradation by blocking of hydrogen bonding sites, and codispersion of starches with fatty materials that complex with amylose.

In a related field, enzymic hydrolysis is a well-established technique in the art for degrading starch to short-chain saccharides as taught, for example, by Leach et al. in U.S. Pat. No. 3,922,196. Reports by J. F. Robyt et al. in Arch. Biochem. Biophys. 122: 8–16 (1967) and K. K. Tung et al., Anal. Biochem. 29: 84–90 (1969) teach that soluble alpha-amylase is characterized by endoenzymic activity and is nonselective in the degradation of the amylose and amylopectin components. It thereby cleaves polymeric starch into a product having a random distribution of molecular chain lengths and properties unlike those of the original components, amylose and amylopectin.

SUMMARY OF THE INVENTION

It has now been unexpectedly found that by immobilizing a water-soluble amylase on an insoluble porous carrier having pore structures preferentially sorptive to amylose over amylopectin, the amylase will preferentially hydrolyze the linear amylose component of an ordinary gelatinized and highly dispersed starch system by an apparently exoenzymic mechanism without significant degradation of the amylopectin.

By virtue of this process, it is an object of the invention to convert ordinary starches into retrogradation-resistant starches of reduced molecular linearity.

It is also an object of this invention to produce amylopectin-like starch products having a high degree of cold water solubility and a reduced tendency to gel in aqueous solutions.

It is another object of this invention to produce starch products having amylose degradation products comprising low molecular weight amylose residues and also short-chain oligosaccharides which are readily separable from the amylopectin.

DETAILED DESCRIPTION OF THE INVENTION

Starchy substrates for use in this invention include all ordinary starches and starch-containing materials which comprise both amylose and amylopectin components. Exemplary of these without limitation thereto are cereal starches and flours such as corn, wheat, rice, etc., and root crop starches and flours such as potato, tapioca, etc. These starches are normally cold-water-insoluble and have an amylose content in the range of about 17–28% by dry weight. It is to be understood, however, that the relative amounts of the amylaceous components in the starting material varies between species and is not critical to the operability of the invention.

Prior to modification, the substrate is dispersed in water or other suitable solvent, such as a 9:1 mixture of dimethyl sulfoxide: water, and heated above the gelatinization temperature for a sufficient time to convert all of the granular starch to a gelatinized and highly dispersed form. Any conventional procedure for dispersion such as prolonged stirring at temperatures above the gelatinization temperature or steam-jet cooking is suitable. Starch dispersion concentrations in the range of about 0.1–5% dry solids basis are preferred, though concentrations as high as about 10% can be employed, provided that the dispersion does not gel or retrograde during the subsequent enzyme modification.

Suitable amylases for degrading the amylose are the alpha-amylases and glucoamylases. Sources for these enzymes include any of the bacterial or fungal microorganisms known to produce them. It is preferred to use alpha-amylase, and that obtained from *Bacillus subtilis* is especially preferred.

The amylases are immobilized by binding them to insoluble porous carriers having pore structures preferentially sorptive to amylose over amylopectin. This property is readily determined by contacting a starch dispersion with an ample supply of the carrier and thereafter measuring the iodine stain intensity of the dispersion. The deep blue color characteristic of stained amylose changes to a purplish color as amylose is removed and the relative proportion of the amylopectin increases. The actual sorptive capacities of the carriers useful in this invention are usually quite small, and it is frequently necessary to repeatedly contact the starch dispersion with fresh samples of carrier in order to remove sufficient amylose for an observable color change in the iodine stain determination. Phenolformaldehyde resins are the preferred carriers for use in the invention. Of course, others having selective amylose sorptivity can also be used, including for example porous glass and porous silica. The ratio of enzyme to carrier will usually range from 1 to 100 mg. of enzyme per gram wet weight of carrier, and preferably about 50 mg./g.

The immobilized amylase is prepared by binding the enzyme to the carrier by any conventional procedure. Phenol-formaldehyde appears to sorb alpha-amylase into its microstructure and bind it by purely physical means. Where the carrier does not lend itself to this mode of immobilization, the enzyme can be bound either by crosslinking to itself or to available reactive sites on the carrier. Preferred crosslinking agents include the dialdehydes, particularly glutaraldehyde. Conditions for dialdehyde crosslinking are well known and are further illustrated in Examples 1–3 below.

The starch dispersions are hydrolyzed by the immobilized amylases under relatively mild conditions. In a batch-type operation, the ratio of enzyme-carrier complex to dry basis starch is in the range of about 5:1–1:5. The complex is kept in suspension by any conventional means such as shaking or stirring and the temperature is held in the range of about 20°–60° C. and optimally at about 40° C. The preferred pH of the dispersion is in the range of 4–5 when the enzyme is glucoamylase, and 6.5–7 when the enzyme is alpha-amylase; though generally the reaction may be conducted anywhere in the pH range of about 3–9. The time period for the reaction is dependent upon factors such as temperature, starch concentration, enzyme potency, and the desired degree of amylose degradation. Generally, the bulk of the modification occurs in the first 1–5 hours, though it continues at a reduced rate for several hours thereafter. For most uses for which the reduction in retrogradation appears to have utility, 1–2 hours is sufficient.

Progress of the reaction and degree of amylose modification can be determined by a variety of procedures as known in the art. One method is determination of reducing power, measured in terms of the percent of hydrolysis of that necessary for conversion of the total polysaccharide content to the theoretical number of glucose units. The instant process can increase reducing power to as much as 6%. Another useful technique is measurement of reduction of color intensity of iodine strain. Reductions on the order of 25–35% are typical for reaction times of 1–2 hours under the above-described conditions. Degree of amylose modification can also be measured in terms of quantity of 80% methyl alcohol solubles, or by molecular size distributions as determined by gel permeation chromatography.

The above-described procedure is a batch operation. Alternatively, a continuous operation could be conducted by passing the starch dispersion through a column of the enzyme-carrier complex or in a series of fluidized-bed reactors with the number of units depending upon the degree of conversion and the rate of production desired.

While not desiring to be bound to any particular mechanism of reaction, it is speculated that those amylose molecules having molecular weights in the range at which retrogradation occurs most readily are preferentially sorbed onto the immobilizing carrier over amylopectin. It is these sorbed molecules that are likely acted upon by the bound enzyme by an exoenzymic pattern of hydrolysis. The hydrolytic products are predominantly amylose residues and short-chain oligosaccharides having a degree of polymerization in the range of 1–8. These relatively small molecules are readily cleared from the carrier, thereby enabling continued amylose sorption and enzymic reaction. Although amylose residues remain after the reaction, the amylose component which is prone to association and retrogradation apparently is effectively removed by degradation.

The extent of penetration of the amylose molecules into the porous microstructure of the carrier is uncertain. Whether the association of the amylose with the carrier is absorption or adsorption is therefore not known. Accordingly, the term "sorb" and its derivatives are used throughout this disclosure in a generic sense intended to describe either situation as appropriate.

The whole enzyme digests separated from the insoluble enzyme-carrier complexes and comprising the retrogradation-resistant starches have potential use in the form of aqueous dispersions or dried solids in a variety of industrial applications. Alternatively, the polysaccharide fraction comprising the amylopectin and amylose residues can be removed from the oligosaccharides and remaining enzyme digest by any conventional procedure such as 80% methyl alcohol precipitation or dialysis. The recovered modified starch can be used in adhesives, foods, papermaking, and most other industrial applications as a substitute for native starch or isolated amylopectin.

The following examples are intended only to further illustrate the invention and are not intended to limit the scope of the invention which is defined by the claims.

EXAMPLE 1

Preparation of immobilized enzyme A.

A soluble *B. subtilis* alpha-amylase was fixed or immobilized onto 200 g. of a phenol-formaldehyde resin (Duolite S-761 manufactured by the Diamond Shamrock Chemical Company) of particulate form (fraction passing a 40-mesh screen and retained on 60 mesh) that had been pretreated by a wash with 0.1M acetate buffer solution (pH 5). The resin was suspended for 3 hours at room temperature in 400 ml. of the buffer that contained 910 mg. of the enzyme. The drained sorption complex was then treated at room temperature in 400 ml. of 1.25% of glutaraldehyde solution for 90 minutes. The enzyme-resin complex was washed with 3 liters of the acetate buffer and with 8 liters of 0.1% soluble starch solution to remove any unbound enzyme.

EXAMPLE 2

Preparation of immobilized enzyme B

A soluble glucoamylase from *Aspergillus niger* was fixed or immobilized onto 20 g. of phenol-formaldehyde resin pretreated as described in Example 1. The resin was suspended in 40 ml. of 0.1M sodium acetate buffer at pH 5.0 that contained 80 units of glucoamylase activity. The mixture was gently agitated at room temperature for about 2 hours and then placed in the refrigerator overnight. A test of the supernatant liquor showed that more than 90% of the glucoamylase had been adsorbed. The enzyme-resin complex was drained and then suspended in 40 ml. of 1.25% glutaraldehyde in the same buffer and held at room temperature for 2 hours. The enzyme-resin complex was filtered and washed on the filter with 5 to 6 liters of water. Further washing was accomplished by suspending the enzyme-resin complex in approximately 1 liter of 0.5% starch solution and shaking on an incubator-shaker for 3 to 4 hours. This was repeated until no further evidence of soluble enzyme was detected (about 10 liters of starch).

EXAMPLE 3

Preparation of immobilized enzyme C

Soluble *B. subtilis* alpha-amylase was fixed or immobilized onto 2 g. of gamma amino propyl silanized glass beads (50–100 mesh, 500 Å pore size). The glass beads were first treated with 5 ml. of 2.5% glutaraldehyde in 0.1M sodium phosphate buffer at pH 7.0 for 1 hour at room temperature. The glutaraldehyde-glass mixture was kept under vacuum to remove air from the pores. The glutaraldehyde-glass was rinsed with water and the drained beads added to 5 ml. of enzyme solutions (20 mg. alpha-amylase/5 ml. of 0.1M sodium phosphate buffer at pH 7.0). After 2 hours at room temperature, the enzyme-glass complex was placed in the refrigerator overnight. A test of the supernatant liquor showed that all but a trace of the enzyme had reacted with the glutaraldehyde-glass beads. The enzyme-glass complex was washed with 2 liters of water followed by 1 liter of 0.1% soluble starch at pH 7.0 to remove any loosely bound enzymes.

EXAMPLE 4

Low shear preparation of substrate dispersions

Two percent and 10% dispersions of gelatinized corn and tapioca starches were prepared by cooking granular starch slurries in distilled water at 90° C. for 1½ hours at low shear in a Corn Industries Research Foundation viscometer.

EXAMPLE 5

Steam-jet cooked preparation of substrate dispersions.

Two percent and 10% dispersions of gelatinized corn starch were prepared by cooking granular starch slurries in distilled water at either 4.2 or 19.5% solids in the hydra-heater section of a continuous steam-jet cooker (Penick and Ford, Ltd.) at a momentary 163° C. temperature with subsequent cooling to about 95° C. after expansion in the flash chamber. Steam pressure to the cooker was 125 p.s.i. and the back pressure in the region past the hydra-heater was 100 p.s.i. Dispersions were diluted to either 2 or 10% concentration and stored at about 70° C. until use.

EXAMPLES 6-19

Preparation of retrogradation-resistant starches

Starch dispersions prepared by the procedures of Examples 4 and 5 were subjected to the phenol-formaldehyde-amylase complexes A and B, prepared in Examples 1 and 2, in various combinations as shown in Table I, below. Flasks containing the immobilized amylases together with the starch dispersions where agitated in a shaking water bath to maintain the enzyme complexes in suspension. The amylase activity was stopped in all cases by filtering of the insoluble enzyme with a coarse, sintered-glass filter. Reaction conditions and results are indicated in Table I.

Reducing powers of the whole enzyme digests were determined on a Technicon Autoanalyzer in Procedure A of Robyt et al. in Anal. Biochem. 45: 517 (1972) using maltose as a standard. Values were expressed as percent of theoretical number of glucose units.

The color intensity of the iodine complexes in enzymic digests was measured essentially by the method of McCready et al. in J. Am. Chem. Soc. 65: 1154 (1943). One-hundred microliters of 0.2% $I_2$ in a 2.0% KI solution were added to the samples which were then diluted to 10 ml. with water. The absorbencies of the solutions at 590 nm. were determined with a Gilford 300-N spectrophotometer.

Intrinsic viscosity measurements of the modified starches precipitated in 80% methanol and reconstituted in 90% dimethyl sulfoxide solution were made at 25° ± 0.05° C. in size 100 Cannon-Ubbelhode capillary viscometers. As shown in Table I, intrinsic viscosities of the starches modified by this invention are not significantly different from those of the control starches.

EXAMPLES 20-23

Controls

For comparative purposes, the reducing powers and iodine intensities of various untreated starch dispersions prepared by the procedures of Examples 4 and 5 were measured, and the results are shown in Table I.

EXAMPLE 24

Control

Example 7 was substantially repeated but without any amylase bound to the phenol-formaldehyde carrier. The reducing power and iodine intensity values shown in Table I indicate that some amylose is sorbed by the carrier but not degraded.

EXAMPLES 25-26

Controls

Ten millimeters of a 2% dispersion of steam-jet cooked corn starch prepared by the process of Example 5 was treated in an Erlenmeyer flask at 40° C. with 50 micrograms of soluble alpha-amylase (without a carrier). Samples were taken at 0.08 hour and 0.25 hour and tested for reducing power and iodine color retention. The results are recorded in Table I. The relatively high reducing power and low iodine color retention values are indicative of extensive and nonpreferential degradation.

EXAMPLE 27

Retrogradation resistance

The modified starches prepared in Examples 6, 7, and 9 were recovered from their respective enzyme digests by 80% methanol precipitation and reconstitution as 6% dispersions in distilled water. These dispersions were kept at 25° C. and their relative viscosities were measured in an Ostwald, Cannon-Fenske capillary viscometer tube at the end of 1, 2, and 3 days as an indication of retrogradation. These results together with those of the unmodified starch control of Example 20 are shown in Table II, below.

It is understood that the foregoing detailed description is given merely by way of illustration and that modification and variations may be made therein without departing from the spirit and scope of the invention.

Table I

| Example | Immobilized enzyme | Substrate[1] | % Substrate in dispersion | Dispersion per amylase complex (g./g.) | Temp. (° C.) | Time (hr.) | pH | Reducing power | % Retention $I_2$ color | Intrinsic viscosity (dl./g.)[2] |
|---|---|---|---|---|---|---|---|---|---|---|
| 6 | A | corn-jc | 2 | 20 | 40 | 1 | 5.25 | 1.44 | 74 | 0.95 |
| 7 | A | corn-jc | 2 | 20 | 40 | 2 | 5.25 | 2.91 | 72 | 0.96 |
| 8 | A | corn-jc | 2 | 20 | 40 | 4 | 5.25 | 2.4 | 66.5 | 0.98 |
| 9 | A | corn-jc | 2 | 20 | 40 | 22 | 5.3 | 6.10 | 40.6 | 0.85 |
| 10 | A | corn-jc | 10 | 20 | 40 | 2 | 5.1 | 2.12 | — | 1.20 |
| 11 | A | corn-jc | 10 | 20 | 40 | 4 | 5.1 | 3.24 | — | 1.17 |
| 12 | A | corn-ls | 2 | 20 | 41 | 0.75 | — | 1.9 | 75.9 | 1.34 |
| 13 | A | corn-ls | 2 | 20 | 41 | 2 | — | 3.2 | 63.0 | 1.47 |
| 14 | A | tapioca-ls | 2 | 20 | 41 | 0.33 | — | 0.19 | 89.5 | 1.79 |

Table I-continued

| Example | Immobilized enzyme | Substrate[1] | % Substrate in dispersion | Dispersion per amylase complex (g./g.) | Temp. (°C.) | Time (hr.) | pH | Reducing power | % Retention I$_2$ color | Intrinsic viscosity (dl./g.)[2] |
|---|---|---|---|---|---|---|---|---|---|---|
| 15 | A | tapioca-ls | 2 | 20 | 41 | 1 | — | 0.58 | 78.0 | 1.78 |
| 16 | A | tapioca-ls | 2 | 20 | 41 | 1.83 | — | 2.64 | 40.2 | 1.60 |
| 17 | A | tapioca-ls | 2 | 20 | 41 | 4 | — | 4.4 | 30.8 | 1.45 |
| 18 | B | corn-jc | 2 | 50 | 40 | 2.5 | 4.2 | 4.14 | 79 | — |
| 19 | B | corn-jc | 2 | 50 | 40 | 3.5 | 4.2 | 7.25 | 68 | — |
| 20 | — | corn-jc | 2 | — | — | — | — | 0 | 100 | 0.95[3] |
| 21 | — | corn-jc | 10 | — | — | — | — | 0 | 100 | 1.14 |
| 22 | — | corn-ls | 2 | — | — | — | — | 0 | 100 | 1.28 |
| 23 | — | tapioca-ls | 2 | — | — | — | — | 0 | 100 | — |
| 24 | — | corn-jc | 2 | — | 40 | 2 | — | 0 | 83 | — |
| 25 | — | corn-jc | 2 | — | 40 | 0.08 | — | 9.56 | 6.4 | — |
| 26 | — | corn-jc | 2 | — | 40 | 0.25 | — | 16.22 | 1.9 | — |

[1] corn-jc = corn-jet cooked; corn-ls = corn-low shear; tapioca-ls = tapioca-low shear.
[2] dl./g. = deciliters/gram.
[3] Average of three controls: 0.905, 0.985, 0.936.

Table II

| Example | Reaction time (hours) | Relative viscosity of 6% dispersion | | |
|---|---|---|---|---|
| | | 1 day | 2 days | 3 days |
| 6 | 1 | 85 | 225 | 380 |
| 7 | 2 | 46 | 55 | 75 |
| 9 | 22 | 25 | 25 | 25 |
| 20 (control) | 0 | gel | gel | gel |

We claim:

1. A method for producing a retrogradation-resistant starch comprising the following steps:
   a. providing a dispersion of a gelatinized starch substrate comprising amylose and amylopectin;
   b. providing an amylase immobilized on an insoluble porous carrier having pore structures preferentially sorptive to amylose over amylopectin wherein said amylase immobilized on an insoluble porous carrier hydrolyzes amylose without significant degradation of amylopectin;
   c. contacting said starch substrate dispersion with said immobilized amylase, under relatively mild hydrolyzing conditions, thereby preferentially hydrolyzing said amylose over said amylopectin, and thereby converting said starch substrate to a retrogradation-resistant starch; and
   d. recovering said retrogradation-resistant starch prepared in step (c).

2. A method as described in claim 1 wherein said starch substrate is selected from the group consisting of cereal starches, cereal flours, root starches, and root flours.

3. A method as described in claim 1 wherein said dispersions are aqueous and said starch substrates are at a dispersion concentration of 0.1-10%.

4. A method as described in claim 1 wherein said porous carrier is selected from the group consisting of phenol-formaldehyde resins, porous glass, and porous silica.

5. The process as described in claim 1 wherein said amylase is selected from the group consisting of alpha-amylase and glucoamylase.

6. The process as claimed in claim 1 wherein said amylase is *B. subtilis* alpha-amylase and said porous carrier is a phenol-formaldehyde resin.

7. The process as described in claim 1 wherein in step (c) said contacting is at a temperature in the range of about 20°-60° C. for a time period of 1-5 hours.

8. The process as described in claim 7 wherein said temperature is about 40° C. and said time period is about 1-2 hours.

9. The process as described in claim 1 wherein said recovering in step (d) comprises separating said retrogradation-resistant starch from said immobilized amylase.

10. The process as described in claim 1 wherein said recovering in step (d) is by precipitation in methyl alcohol.

11. The process as described in claim 1 wherein said recovering in step (d) is by dialysis.

* * * * *